United States Patent [19]

Iwasaki et al.

[11] Patent Number: 5,359,059
[45] Date of Patent: Oct. 25, 1994

[54] PROCESS FOR PREPARING CARBAPENEM DERIVATIVES

[75] Inventors: Tameo Iwasaki, Nishinomiya; Kazuhiko Kondo, Osaka; Hiroshi Horikawa, Kawanishi, all of Japan

[73] Assignee: Tanabe Seiyaku Co., Ltd., Osaka, Japan

[21] Appl. No.: 100,460

[22] Filed: Aug. 2, 1993

[30] Foreign Application Priority Data

Aug. 6, 1992 [JP] Japan .................... 4-209840

[51] Int. Cl.$^5$ ............... C07D 487/04; C07D 499/00
[52] U.S. Cl. ............................ 540/350; 540/310
[58] Field of Search ........................ 540/350

[56] References Cited

U.S. PATENT DOCUMENTS 4,194,047  3/1980  Christensen et al. .

FOREIGN PATENT DOCUMENTS

| 0008497 | 3/1980 | European Pat. Off. . |
| 0057565 | 8/1982 | European Pat. Off. . |
| 160391A | 3/1985 | European Pat. Off. . |
| 0188816 | 12/1985 | European Pat. Off. . |
| 0186525 | 7/1986 | European Pat. Off. . |
| 0256377 | 2/1988 | European Pat. Off. . |
| 0337637 | 3/1989 | European Pat. Off. . |
| 61-5081 | 1/1986 | Japan . |
| 61-18779 | 1/1986 | Japan . |

*Primary Examiner*—Johann Richter
*Assistant Examiner*—Rebecca Cook
*Attorney, Agent, or Firm*—Browdy and Neimark

[57] ABSTRACT

Process for preparing carbapenem derivative of the formula [I], which comprises subjecting azetidinone compound of the formula [II] to intramolecular cyclization reaction together with elimination reaction of the group of —$SR^4$, followed by re-adding said group of —$SR^4$ to the 2-position of the carbapenem skeleton of the intramolecularly cyclized compound, which is industrially useful as process for preparing carbapenem antimicrobials or synthetic intermediate therefor.

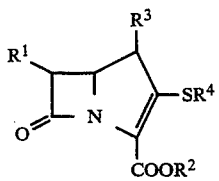

[I]

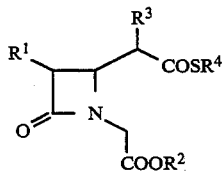

[II]

wherein $R^1$ is protected or unprotected hydroxy-substituted lower alkyl group, $R^2$ is hydrogen atom or ester residue, $R^3$ is hydrogen atom or lower alkyl group, and the group of —$SR^4$ is group which can be used as substituent at 2-position of the carbapenem antimicrobials.

4 Claims, No Drawings

PROCESS FOR PREPARING CARBAPENEM DERIVATIVES

The present invention relates to a novel process for preparing a carbapenem derivative having antimicrobial activity and a synthetic intermediate therefor.

PRIOR ART

There have been known several processes for preparing the carbapenem derivatives which show excellent antimicrobial activities against a wide variety of pathogenic bacteria including Gram-positive and Gram-negative-bacteria, especially against Cephem-resistant bacteria and are stable in the living body. For example, Japanese Patent First Publication (Kokai) No. 103084/1987 discloses a process for preparing a carbapenem antimicrobial which comprises treating a 4-(phenylthiocarbonyl-ethyl)-2-azetidinone derivative with sodium hydride, trapping a by-product, thiol, with an alkylating agent (e.g. iodomethane), further reacting the product with diphenyl chlorophosphate to give a 2-oxycarbapenem derivative, followed by reacting the product with a thiol compound.

BRIEF DESCRIPTION OF THE INVENTION

An object of the present invention is to provide a novel and industrially useful process for preparing a carbapenem antimicrobial and a synthetic intermediate therefor.

DETAILED DESCRIPTION OF THE INVENTION

According to the present invention, a carbapenem derivative of the formula [I]:

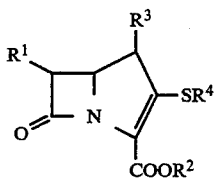

wherein $R^1$ is a protected or unprotected hydroxy-substituted lower alkyl group, $R^2$ is hydrogen atom or an ester residue, $R^3$ is hydrogen atom or a lower alkyl group, and the group of the formula $-SR^4$ is a group which can be used as a substituent at 2-position of the carbapenem antimicrobials, can be prepared by subjecting an azetidinone compound of the formula [II]:

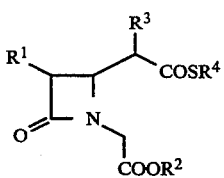

wherein $R^1$, $R^2$, $R^3$ and the group of the formula $-SR^4$ are the same as defined above, or a salt thereof, to intramolecular cyclization reaction together with elimination reaction of a group of the formula $-SR^4$ followed by re-adding said group of the formula $-SR^4$ to the 2-position of the carbapenem skeleton of the intramolecularly cyclized product.

In the present invention, the group represented by $R^1$ is preferably a protected or unprotected 1-hydroxyethyl group, and a protecting group for hydroxy group may be any one which can easily be removed by a conventional removing method, for example, a lower alkoxycarbonyl group, a halogeno-lower alkoxycarbonyl group, a substituted or unsubstituted phenyl-lower alkyl group (e.g. a benzyl which may optionally be substituted by nitro or a lower alkoxy), a tri-lower alkylsilyl group, a substituted or unsubstituted phenyl-lower alkoxycarbonyl group (e.g. a benzyloxycarbonyl which may optionally be substituted by nitro or a lower alkoxy), and the like.

The ester residue represented by $R^2$ is an ester residue which can be metabolized in the living body by hydrolysis, or an ester residue which can be a protecting group for carboxyl group. The ester residue which can be metabolized in the living body by hydrolysis includes groups of the formulae $-X-OCOR^5$, $-X-OCO_2R^5$ and $-X-O-R^5$ wherein X is a lower alkylene group, $R^5$ is a lower alkyl group, a cycloalkyl group, a lower alkenoyl group, a lower alkoxy-lower alkyl group or a lower alkanoyloxy-lower alkyl group, for example, a lower alkanoyloxy-lower alkyl group, a cycloalkanoyloxy-lower alkyl group, a lower alkenoyloxy-lower alkyl group, a lower alkoxy-lower alkanoyloxy-lower alkyl group, a lower alkanoyloxy-lower alkoxy-lower alkyl group, a lower alkoxy-lower alkyl group, a lower alkoxy-lower alkoxy-lower alkyl group, a lower alkoxycarbonyloxy-lower alkyl group and a lower alkoxy-lower alkoxycarbonyloxy-lower alkyl group.

The ester residue which can be a protecting group for carboxyl group includes, for example, a lower alkyl group, a lower alkenyl group, a halogeno-lower alkyl group, nitrobenzyl group and a lower alkoxy-benzhydryl group.

The group represented by $R^3$ is hydrogen atom or a lower alkyl group such as methyl.

The group of the formula $-SR^4$ may be ones which can be a substituent at 2-position of the carbapenem antimicrobials disclosed in Japanese Patent First Publication (Kokai) Nos. 18779/1986, 202886/1985, 5081/1986, 49783/1990, or in U.S. Pat. No. 4,194,047. The group represented by $R^4$ includes, for example, a substituted or unsubstituted lower alkyl group; a substituted or unsubstituted cycloalkyl group; a substituted or unsubstituted 6- to 8-membered aryl group; a substituted or unsubstituted 4- to 8-membered alicyclic heterocyclic group containing a nitrogen atom, an oxygen atom and/or an sulfur atom, or a condensed ring group thereof; a substituted or unsubstituted 4- to 8-membered aromatic heterocyclic group containing a nitrogen atom, an oxygen atom and/or an sulfur atom, or a condensed ring group thereof; and the like. The substituent for these groups includes, for example, a lower alkyl group; hydroxy group; a lower alkoxy group; a mono- or di-lower alkylamino group; a lower alkenoyloxycarbonylamino group; mercapto group; a lower alkylthio group; an imino-lower alkylamino group; amidino group; guanidino group; carbamoyl group; thiocarbamoyl group; sulfamoyl group; cyano group; carboxyl group; a lower alkoxycarbonyl group; an aralkyloxycarbonyl group; oxo group; thioxo group; a halogeno group; a cycloalkyl group; a 6- to 8-membered aryl group; a 4- to 8-membered alicyclic heterocyclic group containing a nitrogen atom, an oxygen atom and/or an sulfur atom, or a condensed ring group thereof; a 4- to 8-membered aromatic heterocyclic group containing a nitrogen atom, an oxygen atom and/or an sulfur atom, or a condensed ring group thereof, and the like. Specific examples of the group represented by $R^4$ are 2-(N-allyloxycarbonylamino)ethyl group, 1,3-thiazol-4-ylmethyl group, thioxopyrrolidinyl group, pyridyl group, and the like.

In the process of the present invention, the intramolecular cyclization reaction of the compound of the formula [II] and the elimination reaction of the group of the formula —$SR^4$ can preferably be carried out by treating the compound [II] with a base and a silylating agent in a suitable solvent. The base includes, for example, a metal salt of an amine [e.g. sodium bis(trimethylsilyl)amide, lithium bis(trimethylsilyl)amide, etc.]; a metal salt of an alcohol (e.g. potassium t-butoxide, etc.); an alkali metal hydride (e.g. sodium hydride, etc.), and the like. The base is usually used in an amount of 1 to 4 equivalents, preferably 2 to 3 equivalents to the starting compound.

The silylating agent includes, for example, a tri-lower alkyl-halogeno-silane (e.g. trimethylchlorosilane, t-butyldimethylchlorosilane, etc.), a tetrahalogenosilane (e.g. tetrachlorosilane, etc.), and the like. The silylating agent is usually used in an amount of 0.1 to 3 equivalents, preferably 1 to 2 equivalents to the starting compound.

The treatment by these bases and silylating agents can preferably be carried out either by treating first the compound [II] with a base, and then with a silylating agent, or vice versa.

The solvent includes, for example, tetrahydrofuran, ethylene glycol dimethyl ether, dioxane, toluene, diethyl ether, benzene, and the like.

The reaction is carried out under cooling or at room temperature, for example, at a temperature from −75° C. to 30° C., preferably at a temperature from −60° C. to 5° C.

The subsequent re-addition reaction of the eliminated group of the formula —$SR^4$ to the 2-position of the carbapenem skeleton of the intramolecularly cyclized product can preferably be carried out by treating the above obtained reaction solution with an active-esterification agent for hydroxy group. The active-esterification agent for hydroxy group includes a reactive derivative (e.g. a corresponding acid halide, a corresponding acid anhydride, etc.) of phosphoric acid compound or sulfonic acid compound such as a diaryl phosphate (e.g. diphenyl phosphate, etc.), a di-lower alkyl phosphate (e.g. diethyl phosphate, etc.), a substituted or unsubstituted lower alkane-sulfonic acid (e.g. methanesulfanic acid, trifluoromethanesulfonic acid, etc.), a substituted or unsubstituted benzenesulfonic acid (e.g. benzenesulfonic acid, p-methoxybenzenesulfonic acid, etc.), and the like. The active-esterification agent for hydroxy group is usually used in an amount of 1 to 3 equivalents, preferably 1 to 1.5 equivalent, to the starting compound.

The re-addition reaction is carried out at the same temperature as defined for the intramolecular cyclization reaction of the compound [II] and the elimination reaction of the group of the formula —$SR^4$ as mentioned above.

In the step of the re-addition reaction of the eliminated group of the formula —$SR^4$ if necessary, the reaction solution obtained by treating with an active-esterification agent for hydroxy group may be treated with a fluoride. The yield of the desired compound [I] can be increased by the fluoride-treatment.

The fluoride includes, for example, an alkali metal fluoride (e.g. potassium fluoride, sodium fluoride, cesium fluoride, etc.); an alkaline earth metal fluoride (e.g. calcium fluoride, etc.), a hydrogenfluoride of inorganic or organic amines (e.g. ammonium fluoride, a tri-lower alkylammonium fluoride, a benzyl-di-lower alkylammonium fluoride, pyridinium fluoride, etc.), and the like. The fluoride is usually used in an amount of 0.1 to 3 equivalents, preferably 0.5 to 1.5 equivalent, to the starting compound.

The starting compound [II] of the present invention can be used in the process of the present invention either in the free form or in the form of a salt thereof. The salt of the compound [II] is, for example, hydrochloride, sulfate, acetate, methanesulfonate, p-toluenesulfonate, and the like.

In the process of the present invention, the starting compound [II] exists in the form of optical isomer owing to the asymmetric carbon thereof. However, when an optically active compound [II] is used in the present process, the compound [II] reacts with maintaining the stereostructure thereof to be converted without epimerization into the desired compound [I].

The resulting carbapenem derivative [I] wherein $R^1$ is the protected hydroxy-substituted lower alkyl group and/or $R^2$ is the ester residue, may be converted to the corresponding carbapenem derivative [I] wherein $R^1$ is the hydroxy-substituted lower alkyl group and/or $R^2$ is hydrogen atom by the removal of the protecting group for the hydroxy-substituted lower alkyl group and/or the ester residue.

Throughout the present description and claims, the "lower alkyl group", the "lower alkylene group", the "lower alkoxy group" and the "lower alkanesulfonic acid" mean ones having 1 to 6 carbon atoms, preferably 1 to 4 carbon atoms, respectively. The "lower alkanoyl group" and the "lower alkenyl group" mean ones having 2 to 8 carbon atoms, preferably 2 to 6 carbon atoms, respectively, and the "lower alkenoyl group" and the "cycloalkyl group" mean ones having 3 to 8 carbon atoms, preferably 3 to 6 carbon atoms, respectively. The "cycloalkanoyl group" means ones having 4 to 9 carbon atoms, preferably 4 to 7 carbon atoms.

The starting compound [II] of the present invention can easily be prepared by a conventional method, for example, by reacting a compound of the formula [III]:

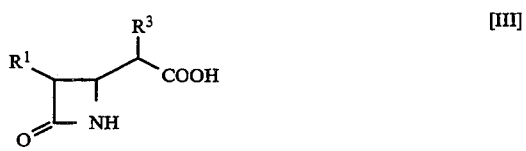

[III]

wherein $R^1$ and $R^3$ are the same as defined above, with a compound of the formula [IV]:

$$Y-CH_2-COOR^2 \qquad [IV]$$

wherein Y is a halogen atom, and $R^2$ is the same as defined above, in the presence of an acid acceptor, followed by reacting the product with a compound of the formula [IV]:

$$H-SR^4 \qquad [V]$$

wherein $R^4$ is the same as defined above, in the presence of a dehydrating agent.

EXAMPLES

The present invention is illustrated in more detail by the following Examples and Reference Example, but should not be construed to be limited thereto.

Example 1

A solution of (3S,4S)-3-[(1R)-1-t-butyldimethylsilyloxyethyl]-4-{(1R)-1-]((4R)-pyrrolidine-2-thion-4-ylthio)carbonyl]-ethyl}-1-(allyloxycarbonylmethyl)-2-azetidinone (1.028 g) in tetrahydrofuran (6 ml) is added dropwise to 1M solution (6.6 ml) of sodium bis(trimethylsilyl)amide in tetrahydrofuran at −60° C. to −50° C. over a period of 5 minutes. The mixture is stirred at −50° C. for 10 minutes, and thereto is added trimethylchlorosilane (0.58 ml) at −60° C. The mixture is stirred at the same temperature for 15 minutes, and thereto is added diphenyl chlorophosphate (0.44 ml) at −60° C. The mixture is stirred at 0° C. for 1.5 hour, and to the reaction mixture is added dimethylformamide (10 ml) at 0° C., and further thereto is added dropwise 1M solution (1.6 ml) of tetra-n-butylammonium fluoride in tetrahydrofuran at −60° C. The mixture is stirred at −50° C. for 30 minutes, and warmed to −20° C. over a period of one hour. After the reaction is complete, the reaction solution is poured into a phosphate buffer (pH 7.0, 20 ml), and the mixture is extracted with ethyl acetate. The aqueous layer is extracted with ethyl acetate, and the ethyl acetate layers are combined, washed twice with water, dried over magnesium sulfate, and concentrated under reduced pressure. The residue is purified by silica gel column chromatography (solvent; n-hexane:chloroform:ethyl acetate=5:5:4) to give (1R,5S,6S)-2-[(4R)-pyrrolidine-2-thion-4-ylthio]-6-](1R)-1-t-butyldimethylsilyloxyethyl]-1-methylcarbapen-2-em-3-carboxylic acid allyl ester (575 mg).

M.p. 130°–133° C.

Examples 2–4

The starting compounds [II-a] listed in Table 1 are treated in the same manner as in Example 1 to give the corresponding desired compounds [I-a].

Example 5

A mixture of (1R,5S,6S)-2-[(4R)-pyrrolidine-2-thion-4-ylthio ]-6-[(1R)-1-t-butyldimethylsilyloxyethyl]-1-methylcarbapen-2-em-3-carboxylic acid allyl ester (1.00 g), dimethylformamide (10 ml) and ammonium hydrogenfluoride (459 mg) is stirred at room temperature for three days. To the reaction solution is added a phosphate buffer (pH 7.0), and the mixture is extracted with ethyl acetate. The organic layer is washed with a phosphate buffer, and the both of the phosphate buffer layers are combined, and extracted with ethyl acetate. The organic layers are combined, washed, dried and concentrated under reduced pressure. The resulting residue is crystallized from a mixture of ethyl acetate and n-hexane (2:1) to give (1R,5S,6S)-2-[(4R)-pyrrolidine-2-thion-4-ylthio]-6-[(1R)-1-hydroxyethyl]-1-methylcarbapen-2-em-3-carboxylic acid allyl ester (657 mg). The filtrate of the above crystallization is concentrated under reduced pressure, and the residue is purified by silica gel flash column chromatography (solvent; chloroform:ethanol=30:1), and further crystallized from a mixture of ethyl acetate and n-hexane (2:1) to give (1R,5S,6S)-2-[(4R)-pyrrolidine-2-thion-4-ylthio]-6-[(1R)-1-hydroxyethyl]-1-methylcarbapen-2-em-3-carboxylic acid allyl ester (24 mg).

Yield: 88.4% M.p. 144°–145° C.

Example 6

A mixture of sodium hydrogen carbonate (0.84 g) in water (10 ml), dimedone (0.84 g) and tetrahydrofuran (80 ml) is treated with ultrasonics, and thereto is added palladium diacetate (0.11 g) and triethyl phosphite (0.58 g) under nitrogen atmosphere, and the mixture is stirred for three minutes. To the mixture is added (1R,5S,6S)-2-[(4R)-pyrrolidine-2-thion-4-ylthio]-6-[(1R)-1-hydroxyethyl]-1-methylcarbapen-2-em-3-carboxylic acid allyl ester (3.83 g), and the mixture is stirred at 35°–37° C. for 45 minutes. The mixture is stirred at 5° C. for 30 minutes, and the precipitated crystals are collected by filtration, washed with tetrahydrofuran, and dried under reduced pressure to give (1R,5S,6S)-2-[(4R)-pyrrolidine-2-thion-4-ylthio]-6-[(1R)-1-hydroxyethyl]-1-methyl-carbapen- 2-em-3-carboxylic acid sodium salt (3.28 g).

TABLE 1

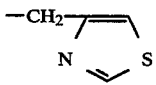

| Ex. No. | $R^2$ | $R^4$ |
|---|---|---|
| 2 | —CH$_2$—CH=CH$_2$ | —CH$_2$CH$_2$NHCO$_2$—CH$_2$CH=CH$_2$ |
| 3 | —CH$_2$—CH=CH$_2$ | 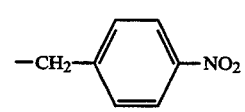 |
| 4 | 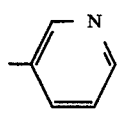 (—CH$_2$—C$_6$H$_4$—NO$_2$) | (pyridyl) |

(TBS:t-butyldimethylsilyl group)

Yield: 90% NMR (D$_2$O) δ: 1.22 (3H, d, J=7 Hz), 1.31 (3H, d, J=6 Hz), 2.87–3.07 (1H, m), 3.20–3.60 (3H, m), 3.55–3.72 (1H, m), 4.05–4.35 (4H, m)

Reference Example 1

(1) (3S,4S)-3-[(1R)-1-t-Butyldimethylsilyloxyethyl]-4-[(1R)-1-carboxyethyl]-2-azetidinone (6 g) is dissolved in tetrahydrofuran (250 ml), and thereto is added 60% sodium hydride (0.796 g) at 10° C., and the mixture is stirred at 20° C. for 20 minutes. To the mixture is added t-butyldimethylsilyl chloride (3 g) at 10° C., and the mixture is stirred for 10 minutes, and concentrated under reduced pressure to the quarter volume thereof. The concentrated mixture is stirred at 20° C. for 20 minutes, and thereto is added a mixture of bromoacetic acid allyl ester (3.56 g) and tetrahydrofuran (190 ml), and further added thereto dropwise 1M solution (20 ml) of sodium bis(trimethylsilyl)amide in tetrahydrofuran at −50° C. The mixture is warmed to 20° C. over a period of 30 minutes, and concentrated under reduced pressure to a quarter volume thereof. The concentrated mixture is stirred at 20° C. for 2 hours, and thereto is added tetrahydrofuran (190 ml), and further added dropwise a solution of potassium carbonate (2.8 g) in water (40 ml) at 10° C. The mixture is stirred at 20° C. for 15 minutes. To the mixture is added diluted hydrochloric acid [hydrochloric acid (4.2 g) in water (8 ml)] at 10° C., and thereto is added 1N hydrochloric acid (18 ml) under ice-cooling. The mixture is allowed to stand, and the organic layer is collected. The aqueous layer is extracted with chloroform, and the organic layers are combined, dried over magnesium sulfate, and concentrated under reduced pressure. The residue is purified by silica gel column chromatography (solvent; chloroform→chloroform:methanol=98:2) to give (3S,4S)-3-[(1R)-1-t-butyldimethylsilyloxyethyl]-4-[(1R)-1-carboxyethyl]-1-(allyloxycarbonylmethyl)-2-azetidinone (5.7 g) as oil.

NMR (CDCl$_3$) δ: 0.0–0.05 (6H, m), 0.78 (9H, s), 1.1–1.25 (6H, m), 2.75–2.90 (1H, m), 2.95–3.02 (1H, m), 4.0–4.12 (2H, m), 3.83, 4.14 (2H, ABq, J=18 Hz), 4.52–4.58 (2H, m), 5.15–5.85 (2H, m), 5.70–5.93 (1H, m)

(2) To a solution of the above product (1 g) in acetonitrile (5 ml) is added a mixture of 4-dimethylaminopyridine (30 mg), (4R)-4-mercaptopyrrolidine-2-thione (336 mg) and dicyclohexylcarbodiimide (632 mg) at 10° C., and the mixture is stirred at the same temperature for 20 hours. The insoluble materials are removed by filtration, and the filtrate is concentrated under reduced pressure. The residue is purified by silica gel column chromatography (solvent; n-hexane:chloroform:ethyl acetate=5:5:4) to give (3S,4S)-3-[(1R)-1-t-butyldimethylsilyloxyethyl]-4-{(1R )-1-[((4R)-pyrrolidine-2-thion-4-ylthio)carbonyl]ethyl}-1-(allyloxycarbonylmethyl)-2-azetidinone (1.073 g) as oil.

NMR (CDCl$_3$) δ: 0.0–0.05 (6H, m), 0.79 (9H, s), 1.1–1.25 (6H, m), 2.7–2.85 (1H, m), 2.90–3.05 (2H, m), 3.15–3.35 (1H, m), 3.40–3.50 (1H, m), 3.96–4.20 (4H, m), 4.18, 3.76 (2H, ABq, J=18 Hz), 4.5–4.6 (2H, m), 5.15–5.35 (2H, m), 5.75–5.95 (1H, m), 8.0–8.12 (1H, br)

Effects of the Invention

According to the present invention, the carbapenem derivative [I], which is useful as a carbapenem antimicrobial and a synthetic intermediate therefor, can industrially advantageously be prepared. More particularly, hitherto, the carbapenem derivatives have been prepared by employing a conventional leaving group instead of the group of the formula —SR$^4$ in the compound [II], subjecting the said compound to cyclization reaction, trapping the leaving group, reacting with a group which is a conventional substituent at 2-position of the carbapenem antimicrobials, and removing a trapped leaving group. On the other hand, in the process of the present invention, the leaving group (—SR$^4$) and the introduced 2-substituent are the same, and hence, the desired compound is obtained without trapping and removing the leaving group. Accordingly, the carbapenem antimicrobials can be obtained more easily by the present process than by the conventional methods.

What is claimed is:

1. A process for preparing a carbapenem derivative of the formula [1]:

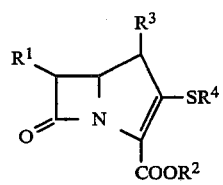

wherein R$^1$ is a protected or unprotected hydroxy-substituted lower alkyl group, R$^2$ is a hydrogen atom or an ester residue, R$^3$ is hydrogen atom or a lower alkyl group, R$^4$ is a substituted or unsubstituted lower alkyl group; a substituted or unsubstituted cycloalkyl group; a substituted or unsubstituted 6- to 8-membered aryl group; a substituted or unsubstituted 4- to 8-membered alicyclic heterocyclic group having a nitrogen atom, an oxygen atom and/or an sulfur atom, or a condensed ring group thereof; a substituted or unsubstituted 4- to 8-membered aromatic heterocyclic group having a nitrogen atom, an oxygen atom and/or a sulfur atom, or a condensed ring group thereof; and the group of the formula —SR$^4$ is a substituent at 2-position of the carbapenem antimicrobials, which comprises treating an azetidinone compound of the formula [II]:

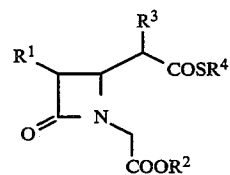

wherein R$^1$, R$^2$, R$^3$ and the group of the formula —SR$^4$ are the same as defined above, or a salt thereof, with a base and a silylating agent, followed by treating with an active-esterification agent for hydroxy group, and when R$^1$ is the protected hydroxy-substituted lower alkyl group and/or R$^2$ is the ester residue, optionally removing the protecting group for the hydroxy-substituted lower alkyl group and/or the ester residue.

2. The process according to claim 1, which comprises treating the product with a fluoride after the treatment with the active-esterification agent for hydroxy group.

3. The process according to claim 1, wherein R$^1$ is a protected or unprotected 1-hydroxyethyl group, R$^3$ is methyl, and R$^4$ is 2-thioxopyrrolidin-4-yl group.

4. The process according to claim 2, wherein R$^1$ is a protected or unprotected 1-hydroxyethyl group, R$^3$ is methyl, and R$^4$ is 2-thioxopyrrolidin-4-yl group.

* * * * *